(12) United States Patent
Czaplewski et al.

(10) Patent No.: US 10,167,818 B2
(45) Date of Patent: *Jan. 1, 2019

(54) MANAGING FUEL OIL MIXTURE IN ENGINES

(71) Applicant: International Business Machines Corporation, Armonk, NY (US)

(72) Inventors: Sarah K. Czaplewski, Rochester, MN (US); Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/849,140

(22) Filed: Dec. 20, 2017

(65) Prior Publication Data

US 2018/0094609 A1    Apr. 5, 2018

Related U.S. Application Data

(63) Continuation of application No. 14/819,667, filed on Aug. 6, 2015.

(51) Int. Cl.
*F02M 25/00* (2006.01)
*G01N 33/28* (2006.01)
(Continued)

(52) U.S. Cl.
CPC .............. *F02M 25/00* (2013.01); *F01M 3/02* (2013.01); *F02D 19/0636* (2013.01);
(Continued)

(58) Field of Classification Search
CPC ............. F02D 19/0634; F02D 19/0636; F02D 19/0649–19/0657; F02D 19/087;
(Continued)

(56) References Cited

U.S. PATENT DOCUMENTS 3,095,692 A    7/1963   Gottlieb
4,452,265 A *  6/1984   Lonnebring ............ B01F 3/088
                                                    137/13
(Continued)

FOREIGN PATENT DOCUMENTS

JP    2001-303918 A    10/2001
JP    2004-285977 A    10/2004

OTHER PUBLICATIONS

"Right Mix Strips™: Know your mix," fullspeedtechnology.com, 3 pages, printed Aug. 4, 2015, © Fullspeed Technology Inc., http://www.fullspeedtechnology.com/right-mix-stripstrade.html.
(Continued)

*Primary Examiner* — Stephen K Cronin
*Assistant Examiner* — Robert Werner
(74) *Attorney, Agent, or Firm* — Nathan M. Rau

(57) ABSTRACT

A fuel tank containing a fuel and oil mixture is managed to determine if the fuel and oil mixture contains the correct ratio for a motor. The fuel tank containing a fuel and oil mixture is monitored. A fuel to oil ratio is selected for the motor. A combined viscosity of the fuel and oil mixture is calculated with respect to the fuel to oil ratio, and the temperature of the fuel and oil mixture. The combined viscosity is used to determine a predetermined range of the combined viscosity. The viscosity of the fuel and oil mixture within the fuel tank is measured as a measured viscosity. If the measured viscosity of the fuel and oil mixture does not correspond with the predetermined range, then a user may be alerted that the measured viscosity does not correspond with the predetermined range.

1 Claim, 4 Drawing Sheets

(51) Int. Cl.
   F02D 19/06      (2006.01)
   F02D 19/08      (2006.01)
   F01M 3/02       (2006.01)
   G01N 11/00      (2006.01)
   F02D 41/22      (2006.01)

(52) U.S. Cl.
   CPC ....... *F02D 19/0649* (2013.01); *F02D 19/087* (2013.01); *G01N 33/2835* (2013.01); *F02D 19/0623* (2013.01); *F02D 2041/228* (2013.01); *G01N 11/00* (2013.01); *Y02T 10/36* (2013.01)

(58) Field of Classification Search
   CPC ............ F01M 3/00–3/02; F02M 25/00; G01N 33/2829; G01N 33/35; G01N 33/2888
   USPC ..................... 123/73 AD, 575, 1 A
   See application file for complete search history.

(56) References Cited

U.S. PATENT DOCUMENTS

| | | | |
|---|---|---|---|
| 4,614,438 A | 9/1986 | Kobayashi | |
| 5,370,089 A * | 12/1994 | Harada | F01M 3/02 |
| | | | 123/196 M |
| 5,460,713 A | 10/1995 | Takito et al. | |
| 6,820,584 B2 | 11/2004 | Koerner et al. | |
| 6,935,311 B2 | 8/2005 | Visser et al. | |
| 8,244,496 B2 | 8/2012 | Kumagai et al. | |
| 8,450,253 B2 | 5/2013 | Komatsubara | |
| 8,584,657 B2 * | 11/2013 | Yagi | F02D 19/0628 |
| | | | 123/1 A |
| 8,679,202 B2 | 3/2014 | Eaton et al. | |
| 9,689,320 B2 * | 6/2017 | Yagi | F02D 19/0605 |
| 2008/0153726 A1 | 6/2008 | Damm et al. | |
| 2010/0099591 A1 | 4/2010 | Harrold et al. | |
| 2011/0000549 A1 | 1/2011 | Yagi et al. | |
| 2011/0259294 A1 | 10/2011 | Herzer et al. | |
| 2013/0080022 A1 | 3/2013 | McDonald | |
| 2013/0143782 A1 | 6/2013 | Baillargeon et al. | |
| 2015/0128919 A1 | 5/2015 | Ibrahim | |

OTHER PUBLICATIONS

"Japanese team names XL7 "viscometer of choice" for petroleum characterisation," hydramotion.com, 2 pages, printed: Aug. 4, 2015, http://www.hydramotion.com/news_JapanEnergy.html.

"Mixing Oils," Mixing viscosities calculator, Widman International, 1 page, printed Aug. 4, 2015, http://www.widman.biz/English/Calculators/Mixtures.html.

"Guidelines for Diesel Engines Lubrication—Oil Degradation", The International Council on Combustion Engines, Apr. 2004, 66 pages.

Definition for "Distilate Fuel Oil", United States Energy Information Administration, retrieved from http://www.eia.gov/tools/glossary/index.cfm?id=distillate%20fuel%20oil, Printed Jan. 23, 2017, 1 page.

Yvonne, T., "Diesel Fuel's Role as a Lubricant," Petroleum Equipment & Technology Archive, Posted: Jan. 5, 2000, Issued: May 2000, pp. 1-6.

Velaers, A., "2-Stroke Oil in Diesel—A Technical Study," 11th International Tribology Conference—SAIT Tribology 2015, Paper ID: SAIT2015-011, Mar. 10, 2015, pp. 1-10.

Czaplewski et al., "Managing Fuel Oil Mixture in Engines," U.S. Appl. No. 14/819,667, filed Aug. 6, 2015.

Czaplewski et al., "Managing Fuel Oil Mixture in Engines," U.S. Appl. No. 14/974,603, filed Dec. 18, 2015.

Accelerated Examination Support Document dated Dec. 16, 2015 for U.S. Appl. No. 14/974,603, 7 pages.

Czaplewski et al., "Managing Fuel Oil Mixture in Engines," U.S. Appl. No. 15/849,059, filed Dec. 20, 2017.

Czaplewski et al., "Managing Fuel Oil Mixture in Engines," U.S. Appl. No. 15/849,100, filed Dec. 20, 2017.

List of IBM Patents or Patent Applications Treated as Related, signed Dec. 20, 2017, 2 pages.

* cited by examiner

| ARTIC FIRE AT 40°C ||||| SABER AT 40°C |||||
|---|---|---|---|---|---|---|---|---|---|
| VISCOSITY OF FUEL (cSt) | VISCOSITY OF OIL (cSt) | FUEL:OIL RATIO | COMBINED VISCOSITY (cSt) | | VISCOSITY OF FUEL (cSt) | VISCOSITY OF OIL (cSt) | FUEL:OIL RATIO | COMBINED VISCOSITY (cSt) | |
| 0.6 | 30.5 | 20:1 | 0.878 | | 0.6 | 71 | 20:1 | 1.025 | |
| 0.6 | 30.5 | 40:1 | 0.730 | | 0.6 | 71 | 40:1 | 0.794 | |
| 0.6 | 30.5 | 50:1 | 0.703 | | 0.6 | 71 | 50:1 | 0.752 | |
| 0.6 | 30.5 | 80:1 | 0.663 | | 0.6 | 71 | 80:1 | 0.692 | |
| 0.6 | 30.5 | 100:1 | 0.650 | | 0.6 | 71 | 100:1 | 0.673 | |

| ARTIC FIRE AT 100°C ||||| SABER AT 100°C |||||
|---|---|---|---|---|---|---|---|---|---|
| VISCOSITY OF FUEL (cSt) | VISCOSITY OF OIL (cSt) | FUEL:OIL RATIO | COMBINED VISCOSITY (cSt) | | VISCOSITY OF FUEL (cSt) | VISCOSITY OF OIL (cSt) | FUEL:OIL RATIO | COMBINED VISCOSITY (cSt) | |
| 0.6 | 6.17 | 20:1 | 0.712 | | 0.6 | 11.1 | 20:1 | 0.761 | |
| 0.6 | 6.17 | 40:1 | 0.654 | | 0.6 | 11.1 | 40:1 | 0.677 | |
| 0.6 | 6.17 | 50:1 | 0.643 | | 0.6 | 11.1 | 50:1 | 0.661 | |
| 0.6 | 6.17 | 80:1 | 0.627 | | 0.6 | 11.1 | 80:1 | 0.638 | |
| 0.6 | 6.17 | 100:1 | 0.621 | | 0.6 | 11.1 | 100:1 | 0.630 | |

FIG. 3

MANAGING FUEL OIL MIXTURE IN ENGINES

BACKGROUND

The present disclosure relates to fluid handling, and more particular aspects relate to monitoring the mixture of a fluid using viscosity.

Internal combustion engines turn a combustion of fuel into electrical and mechanical energy. Certain internal combustion engines have different power cycles (e.g., four stroke and two stroke). Internal combustion engines require lubrication while operating to prevent wear during operation. The fuel is compressed by a cylinder, ignited by a spark plug, and exhausted. Igniting the fuel and oil (fuel:oil, fuel to oil) mixture drives the cylinder downward, which turns a crankshaft. The crankshaft transfers the energy created by the ignition of the fuel to propel a machine housing the internal combustion engine.

SUMMARY

According to embodiments of the present disclosure, a method, a system, and a computer program product is proposed to monitor a viscosity of a fuel and oil mixture within a fuel tank. The fuel and oil mixture may contain a fuel, and an oil mixed in a fuel to oil ratio that corresponds to a fuel to oil ratio of an internal combustion engine. The temperature and a viscosity of the fuel and oil mixture may be measured to determine if the fuel and oil mixture corresponds with the fuel to oil ratio of the internal combustion engine.

One embodiment provides a method for managing a fuel tank containing a fuel and oil mixture to determine if the fuel and oil mixture contains the correct ratio for a motor. The fuel tank containing a fuel and oil mixture is monitored. A fuel to oil ratio is selected for the motor. A combined viscosity of the fuel and oil mixture is calculated with respect to the fuel to oil ratio, and the temperature of the fuel and oil mixture. The combined viscosity is used to determine a predetermined range of the combined viscosity. The viscosity of the fuel and oil mixture within the fuel tank is measured as a measured viscosity. If the measured viscosity of the fuel and oil mixture does not correspond with the predetermined range, then a user may be alerted that the measured viscosity does not correspond with the predetermined range.

Another embodiment is directed toward a system for managing a fuel tank containing a fuel and oil mixture to determine if the fuel and oil mixture contains the correct ratio for a motor. The system includes a memory, a processor device communicatively coupled to the memory, and a sensor module communicatively coupled to the processor device. The sensor module contains a measurement tool, a computing tool, and an alert tool. The measurement tool of the sensor module are configured to monitor the fuel tank containing a fuel and oil mixture. The computing tool of the sensor module are configured to select a fuel to oil ratio for the motor. The computing tool of the sensor module are configured to calculate a combined viscosity of the fuel and oil mixture with respect to the fuel to oil ratio, and the temperature of the fuel and oil mixture. The computing tool of the sensor module are configured to determine a predetermined range of the combined viscosity. The measurement tool of the sensor module are configured to measure the viscosity of the fuel and oil mixture within the fuel tank as a measured viscosity. The alert tool of the sensor module are configured to alert a user if the measured viscosity of the fuel and oil mixture does not correspond with the predetermined range.

Yet another embodiment is directed toward a computer program product for managing a fuel tank containing a fuel and oil mixture to determine if the fuel and oil mixture contains the correct ratio for a motor. The computer program product is configured to monitor the fuel tank containing a fuel and oil mixture. The computer program product is configured to select a fuel to oil ratio for the motor. The computer program product is configured to calculate a combined viscosity of the fuel and oil mixture with respect to the fuel to oil ratio, and the temperature of the fuel and oil mixture. The computer program product is configured to determine a predetermined range of the combined viscosity. The computer program product measures the viscosity of the fuel and oil mixture within the fuel tank as a measured viscosity. The computer program product is configured to alert a user if the measured viscosity of the fuel and oil mixture does not correspond with the predetermined range.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 3 depicts tables of the combined viscosity of a fuel:oil ratio with respect to temperature, according to embodiments.

Figure 1A:
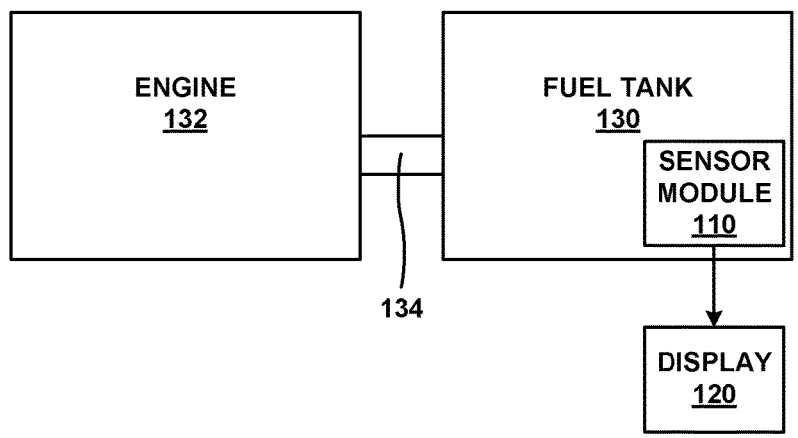
FIG. 1A depicts an illustration of a fuel tank with a sensor module monitoring the fuel to oil ratio, according to various embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to monitoring a fuel to oil ratio, more particular aspects relate to monitoring a viscosity of the fuel to oil ratio of a two-stroke internal combustion engine. The fuel to oil ratio is monitored to determine a proper fuel and oil mixture within the fuel tank of the two-stroke engine. The fuel to oil ratio may be monitored using a viscometer measuring the viscosity of a fuel to oil mixture. While the present disclosure is not necessarily limited to such applications, various aspects of the disclosure may be appreciated through a discussion of various examples using this context.

A two-stroke engine (two-cycle engine, 2-stroke engine) requires a mixture of a fuel and an oil to lubricate the crankshaft during operation. The fuel and oil mixture is used to lubricate the crankshaft because two-stroke engines do not have oil reservoirs to lubricate the crankshaft. A fuel and oil mixture may be a mixture of a first fuel and a first oil combined at a predetermined value for the two-stroke engine. For example, a fuel and oil mixture may be 1 fluid ounce (fl. oz.) oil to 100 fl. oz. fuel. Different two-stroke engines require certain mixtures of fuel and oil for operation. The type or style of the two-stroke engine may require a user to select the fuel:oil ratio for the machine based on the manufacturer's specifications. The fuel and oil mixture can be given the form of a fuel to oil ratio (fuel:oil ratio), which may be achieved by mixing an amount of fuel with an amount of oil. The fuel:oil ratio may be a predetermined value of the amount of fuel and oil that may be mixed together. For example, a fuel oil ratio may include a 1 part oil in 100 part fuel ratio (100:1, 1% oil). To prevent the two-stroke engine from being damaged during operation, oil may need to be added to the fuel. To be able to monitor if the oil has been added to the fuel, a viscometer may be used. The viscometer may measure the contents of a fuel tank to determine the fuel:oil ratio. The fuel tank may be a reservoir that stores the fuel to oil mixture before entering a fuel line to be injected into the engine. For example, the fuel tank may be a two-liter liquid reservoir for storing the fuel and oil mixture. The viscometer may send the determination to a computer with an alert system, and the alert system may alert a user if the fuel:oil ratio of the contents in the fuel tank does not correspond with a predetermined range for the engine. For example, if the oil is not mixed with the fuel or the mixture of fuel to oil is too low, then engine damage may occur due to piston seizures. In another example, if the oil is added in excess, then the spark plug which ignites the fuel and oil mixture may become fouled (e.g., fail due to a buildup of oil on the plug). The exhaust of the fuel to oil mixture may also increase in hydrocarbon emissions if the oil is added in excess.

Two-stroke internal combustion engines (two-stroke engines) may be utilized to take advantage of the power-to-weight ratio. Typically two-stroke engines, when compared to four-stroke engines, have an increased power-to-weight ratio. For example, where a two-stroke engine and a four-stroke engine both have the same power output, the weight of the two-stroke engine typically is less than the four-stroke engine.

Fuel may be a material that stores potential energy that may be released to produce work or heat energy. The fuel may be burned or ignited though combustion to produce energy in the form of work. Work may include producing mechanical energy to perform a function. Fuel may include solid fuels, liquid fuels, gaseous fuels, biofuels, and fossil fuels. Fossil fuels may be refined into solid fuel, liquid fuel, or gaseous fuels. Liquid fuels may include gasoline (petrol) derived from petroleum, which is itself refined from crude oil (fossil fuels). Gasoline may be burned in an internal combustion engine as the fuel. The burning of gasoline within an internal combustion engine produces energy in the form or work, which may be transformed into mechanical energy to perform a function. The function may be determined by the machine that contains the internal combustion engine burning the fuel. Machines will be described further herein.

Oil (engine oil, motor oil) may be a neutral nonpolar chemical substance that may be used for lubrication in internal combustion engines. Motor oils may be derived from petroleum-based compounds or non-petroleum-synthesized chemical compounds (e.g., synthetic motor oil). Motor oils lubricate the internal combustion engine to reduce wear on moving parts.

The fuel:oil ratio may include mixing a volume of fuel with a volume of oil. An example of a fuel:oil ratio may include a 50:1 fuel:oil ratio, where 50 parts of fuel are mixed with 1 part of oil. The 50:1 fuel:oil ratio may include a liquid mixture of 1 gallon (gal) of fuel to 2.5 fluid ounces (fl. oz.) of oil (i.e. 128:2.5 fl. oz.). The fuel:oil ratio may also be shown as a percentage. For example, a 50:1 fuel:oil ratio would be 2% oil mixed with 98% fuel.

The fuel:oil ratio may be measured within the fuel tank with a viscometer to determine if the fuel:oil ratio corresponds with a predetermined range. The viscosity measures the resistance of a liquid to shear or tensile stress. Kinematic viscosity may be used to measure the dynamic viscosity of the fluid with respect to the density. Kinematic viscosity and viscosity will be used interchangeably herein. The measurement of viscosity may be recorded in centistokes (cSt) or millimeter squared per second (mm$^2$/s) (i.e. m$^2$/s×10$^{-6}$). For example, the viscosity of water at 20° C. is approximately 1.004 cSt. Depending on the fuel and the oil, the viscosity may differ. For example, AMSOIL SABER® synthetic 2-stroke oil (property of AMSOIL Incorporated) has a viscosity of 71 cSt at 40° C., whereas Sinclair Artic Fire® 2-cycle engine oil (property of Sinclair Oil Corporation) has a viscosity of 30.56 cSt at 40° C.

The viscosity of the fuel and oil mixture may be measured to determine if the fuel:oil ratio is corresponds with a predetermined range. The viscosity of the fuel and oil mixture may be measured with a viscometer. This viscometer may communicate with a computer that may display the viscosity of the fuel and oil mixture. The computer may also display a fuel:oil ratio of the fuel oil mixture. The computer may alert the user that the fuel:oil ratio of the fuel and oil mixture does not correspond with the predetermined range of a calculated fuel:oil ratio. For example, the calculated viscosity is 1.0 cSt with a predetermined range of ±0.1 cSt. If the measured viscosity of the fuel and oil mixture is 1.05 cSt, then the measured fuel and oil mixture corresponds with the predetermined range. In an additional example, the calculated viscosity is 1.0 cSt with a predetermined range of ±0.1 cSt. If the measured viscosity of the fuel and oil mixture is 1.15 cSt, then the measured fuel and oil mixture does not correspond with the predetermined range and an alert may be generated.

The viscometer may operate in conjunction with a temperature sensor module due to a relationship between viscosity and temperature. Depending on the fluid, changes in temperature affect the viscosity of the fluid. For example, the viscosity of water at 10° C. is approximately 1.307 cSt which is higher than the viscosity of water at 20° C. (approximately 1.004 cSt). In another example, AMSOIL SABER® synthetic 2-stroke oil has a viscosity of 71 cSt at 40° C., but a viscosity of 11.1 cSt at 100° C. In another example, Sinclair Artic Fire® two-stroke oil has a viscosity of 30.56 cSt at 40° C., but a viscosity of 6.17 cSt at 100° C.

The viscosity of unleaded gasoline may typically range between 0.5 and 0.75 cSt at 40° C. depending on the manufacturer of the fuel. Typically, when an oil is more viscous, the recommended fuel and oil mixture ratio increases. For example, the recommended mixture of fuel:oil ratio for SABER®, a higher viscosity oil compared to Artic Fire®, is 80:1 or 100:1 whereas the recommended mixture fuel:oil ratio for Arctic Fire® is 50:1 and below.

The predetermined range may include an area of variation between an upper threshold and a lower threshold of the fuel:oil ratio. The predetermined range may be determined by calculating a viscosity based on the oil and the fuel to be mixed. The calculated viscosity may then be given an upper threshold and a lower threshold as a predetermined range that the fuel:oil ratio may be within without generating an alert. The predetermined range may also be a first threshold which, when reached, generates an alert. The first threshold may be determined by the viscosity of the fuel, the viscosity of the oil, and the recommended fuel:oil ratio of the machine. For example, a fuel:oil ratio with a viscosity of 1.1 cSt may be initialized with a predetermined range of ±0.2 cSt. An alert of the upper threshold being reached may be generated if the viscosity of the fuel:oil ratio is 1.3 cSt or above. An alert of the lower threshold being reached may be generated if the viscosity of the fuel:oil ratio is 0.9 cSt or below.

In various embodiments, the predetermined range may be dynamically calculated. The dynamically calculated range may include a percentage that is used to calculate a dynamic range. The calculated dynamic range may be a large range when the calculated viscosity is high, and the dynamic range may be small if the viscosity is low. The dynamic viscosity may include a set percentage that causes the dynamic range to change. The dynamic viscosity may be calculated from a percentage deviation from the calculated viscosity. For example, for a high viscosity fuel and oil mixture the dynamic range may be calculated from a 10% deviation, and if the calculated viscosity is 1.0 cSt, then the dynamic range may be ±0.1 cSt. The upper threshold may then be 1.1 cSt and the lower threshold may then be 0.9 cSt. In another example, for a low viscosity fuel and oil mixture the dynamic range may be calculated from a 10% deviation, and if the calculated viscosity is 0.7 cSt, then the dynamic range may be ±0.07 cSt. The upper threshold may then be 0.77 cSt and the lower threshold may then be 0.73 cSt.

The alert may include a visual or audible system that informs a user upon the determination that the fuel:oil ratio does not correspond with the predetermined range. Examples of alerts may include but are not limited to a light emitting indicator and/or a sound emitting indicator. A light emitting indicator could include a warning light or a display. A sound emitting indicator could include a buzzer or alarm. If the viscosity of the fuel and oil mixture does not correspond with the predetermined range, then an alert may be generated. For example, the alert may include an audible alert that makes a sound or tone if the viscosity of the fuel and oil mixture does not correspond with the predetermined range. In an additional example, the alert may include a warning light, which is illuminated when the viscosity of the fuel and oil mixture does not correspond with the predetermined range.

The user may be informed about the viscosity of the fuel and oil mixture not corresponding with the predetermined range. Informing the user may include informing the user to add more oil to the fuel and oil mixture. Informing the user may include informing the user to add more fuel to the fuel and oil mixture. For example, the calculated fuel:oil ratio is 1.0 cSt with a predetermined range of ±0.1 cSt. If the measured viscosity is 1.15 cSt, then the user may be informed to add additional fuel to the fuel and oil mixture. In an additional example, the calculated fuel:oil ratio is 1.0 cSt with a predetermined range of ±0.1 cSt. If the measured viscosity is 0.85 cSt, then the user may be informed to add additional oil to the fuel and oil mixture.

To determine a calculated viscosity for the fuel:oil range the Gambill Method may be used. The Gambill Method:

$$V_c^{1/3} = X_f V_f^{1/3} + X_o V_o^{1/3}$$

The Gambill Method can be used to calculate the measurement of the combined viscosity ($V_c$). The combined viscosity may be calculated using the mass fraction of the fuel ($X_f$), the mass fraction of the oil ($X_o$), the viscosity of the fuel ($V_f$), and the viscosity of the oil ($V_o$). For the Gambill Method to be calculated, the viscosity at the temperature needs to be known. To gather the viscosity at a temperature a lookup table may be used. If the temperature of the fuel:oil ratio is 55° C. then the viscosities of the fuel and the oil may be acquired from the lookup table at 55° C. If the viscosity for the oil at 55° C. is 45 cSt, then the $V_o$ in the Gambill method may be 45 cSt. If the viscosity for the fuel at 55° C. is 0.65 cSt, then the $V_f$ in the Gambill method may be 0.65 cSt. Using the Gambill method of the fuel and oil at 55° C., the $V_c$ at a 40:1 fuel:oil ratio may be 0.844 cSt.

The lookup table may also include a repository of the combined viscosities for the fuel and oil mixture for various temperatures. The lookup table may be a stored repository within a computer that can be used to determine if the measured viscosity of the fuel and oil mixture corresponds with the predetermined range of the combined viscosity. For example, a fuel and oil mixture may have a lookup table including a range from −20° C. to 100° C. The lookup table may include a combined viscosity measurement for the fuel and oil mixture for every 1° C. change within the range of −20° C. to 100° C. In an additional example, the fuel oil mixture may have a combined viscosity measurement for every 0.1° C. change within the range of −20° C. to 100° C. The lookup table may then be referenced to determine if the measured viscosity of the fuel and oil mixture corresponds with the predetermined range of the combined viscosity stored on the look up table.

In various embodiments, the alert may be displayed on a device, which may be used by a user to determine the fuel:oil ratio. The device may display the fuel:oil ratio within the fuel tank. For example, the device may be a graphical user interface (GUI). The GUI may display the current fuel:oil ratio based on the viscosity of the fuel and oil mixture. In another example, the alert may communicate wirelessly with a device, where the device displays the alert to the user.

In various embodiments, the alert may inform the user to add either more oil or fuel to the mixture depending on the fuel:oil ratio. If the fuel:oil ratio is determined to not correspond with the predetermined range, the alert may inform the user to add more fuel or oil to the mixture. For example, if the lower threshold is reached, indicating that not enough oil is within the fuel:oil ratio, the alert may inform the user to add more oil.

In various embodiments, a second lower threshold may be included with the alert or may generate a second alert. The second threshold may determine if oil was not mixed with the fuel before being added to the fuel tank. The second threshold may be determined by the viscosity of the fuel, the viscosity of the oil, and the recommended fuel:oil ratio of the machine. For example, if the viscosity of the fuel is 0.6 cSt, then a second lower threshold may be placed on the fuel:oil ratio at 0.65 cSt. If the viscosity of the fuel and oil mixture is 0.64 cSt, then the alert may be generated informing the user that oil has not been added to the fuel and oil mixture.

FIG. 1A depicts an illustration of a fuel tank with a sensor module monitoring the fuel:oil ratio, according to embodiments. The sensor module 110 may monitor the viscosity and the temperature of the fuel and oil mixture. The fuel tank 130 may include a sensor module 110 communicatively coupled with a display 120. The sensor module 110 may determine the fuel:oil ratio of the contents (i.e. fuel and oil mixture) of the fuel tank 130. The fuel tank 130 may distribute the fuel and oil mixture from the tank to the engine 132 through the fuel line 134. The sensor module 110 may include a viscometer. The viscometer of the sensor module 110 may measure the viscosity of the fuel and oil mixture within the fuel tank 130. The sensor module 110 may also include a temperature sensor that measures the temperature of the fuel and oil mixture within the tank. For example, the sensor module 110 may measure a viscosity of 1.1 cSt and the temperature of 45° C.

The sensor module 110 may include a computing system that may calculate a predetermined range of acceptable viscosities that the measured viscosity may be within, without triggering an alert. The computing system may continuously calculate the predetermined range of acceptable viscosities based on the fuel:oil ratio, the temperature of the mixture within the fuel tank 130, the type of oil, and the type of fuel. Before the predetermined range of viscosities is calculated, the type of oil and the type of fuel may need to be inputted into the computer. The computer may store the fuel:oil ratio for the engine and measure the temperature. The predetermined range may be adjustable or dynamic based on the engine 132. For example, if the temperature is 45° C. and the computing system calculates based on the fuel, the oil, and the fuel:oil ratio that the viscosity should be 1.15 cSt, then a possible predetermined range may be ±0.1 cSt. If the predetermined range is ±0.1 cSt at 45° C., then the measured viscosity can be between 1.05 cSt and 1.25 cSt. If the measured viscosity is 1.1 cSt, then the measured viscosity corresponds with the predetermined range.

The display 120 may communicatively couple with the sensor module 110 and include an input system where the user may input the fuel:oil ratio of the engine, the type of fuel, and the type of oil. The fuel:oil ratio for example may include a 20:1, a 40:1, a 50:1, an 80:1, or a 100:1 ratio. The type of fuel may include various octane levels of gasoline. The type of oil may include the brand of the oil or the user may input two oil viscosities of the oil at two temperatures. The computing system of the sensor module may store information for each of the two cycle engine oils. For example, the user may input AMSOIL SABER® as the oil. The information stored on the computing system can then use the viscosities stored on a lookup table to determine if the fuel:oil ratio corresponds with the predetermined range. The user may input two viscosities of the oil at two respective temperatures. For example, the user may input for AMSOIL SABER® a first viscosity of 71 cSt at 40° C., and a second viscosity of 11.1 cSt at 100° C., after which the lookup table may create a new entry for the calculated viscosity, and the predetermined ranges.

In various embodiments, the sensor module 110 may be located within the fuel line 134 between the fuel tank 130 and the engine 132. The sensor module 110 may be placed just before the fuel is turned into an air and gas mixture. The sensor module 110 within the fuel line may measure the viscosity, the temperature, and the pressure of the fuel and oil mixture within the fuel line. If the sensor module 110 is within the fuel line 134, then the sensor module 110 may also include a pressure sensor. The pressure sensor may be used to adjust the viscosity based on the pressure within the fuel line 134.

In various embodiments, the sensor module 110 may be a stand-alone device and placed within the fuel tank 130 when needed. The stand-alone sensor module 110 may be placed in the tank to determine the viscosity and the temperature, and may be removed after the determination. For example, the stand-alone sensor module 110 may be inserted within the fuel tank 130 through a fuel nozzle, the stand-alone sensor module may determine the fuel:oil ratio of the fuel and oil mixture, and may be removed after the determination. The sensor module may also include a display 120 where a user may input the fuel:oil ratio of the engine, the type of fuel, and the type of oil. The display 120 may display the viscosity of the fuel:oil ratio.

Figure 1B:
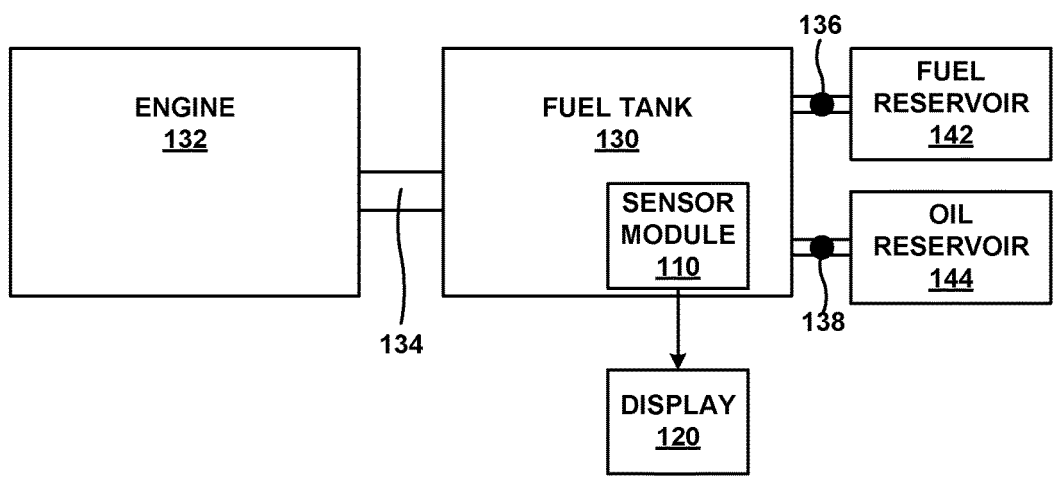
FIG. 1B depicts an illustration of a fuel tank with a sensor module monitoring the fuel to oil ratio with a fuel reservoir and an oil reservoir, according to various embodiments.

FIG. 1B depicts an illustration of a fuel tank with a supplemental fuel reservoir and a supplemental oil reservoir, according to embodiments. Upon a determination using the sensor module 110 that viscosity of the fuel and oil mixture does not correspond with the predetermined range, fuel or oil may be added to the fuel and oil mixture within the fuel tank 130. The fuel reservoir 142 may store a portion of unadulterated fuel to be added to the fuel and oil mixture if the sensor module 110 determines that the viscosity of the fuel and oil mixture is too viscous. If the fuel and oil mixture is too viscous, then additional fuel may be added to the fuel and oil mixture through a fuel pump 136. For example, a calculated viscosity from the fuel and the oil at a temperature may be 0.78 cSt with a predetermined range of ±0.05 cSt. If the actual viscosity of the fuel and oil mixture is 0.90 cSt, then fuel may be added to reduce the viscosity of the fuel and oil mixture. The oil reservoir 144 may store a portion of unadulterated oil to be added to the fuel and oil mixture if the sensor module 110 determines that the viscosity of the fuel and oil mixture is not viscous enough. If the fuel and oil mixture is not viscous enough, then additional oil may be added to the fuel and oil mixture through an oil pump 138. For example, a calculated viscosity from the fuel and the oil at a temperature may be 0.78 cSt with a predetermined range of ±0.05 cSt. If the actual viscosity of the fuel and oil mixture is 0.70 cSt, then oil may be added to increase the viscosity of the fuel and oil mixture.

The fuel reservoir 142 may store a portion of fuel that may be added to the fuel and oil mixture. The fuel reservoir 142 may store the same or similar fuel as used when making the fuel oil mixture for the fuel tank 130. The fuel may be an unadulterated fuel, which may include a fuel that has not been premixed with an oil. For example, a user may create the fuel and oil mixture from a first fuel and a first oil and fill the fuel reservoir 142 with the first fuel. The fuel and oil mixture may be put into the fuel tank 130. An additional portion of the unadulterated first fuel (has not been mixed with the first oil) may be put into the fuel reservoir 142.

In various embodiments, the additional portion of the unadulterated fuel may include a predetermined portion of fuel. The predetermined portion of fuel may include adding a measured amount of fuel to the fuel and oil mixture. If the viscosity of the fuel and oil mixture is does not correspond with the predetermined range, then one or more predetermined portions of fuel may be added until the viscosity of the fuel and oil mixture corresponds with the predetermined range. To cause the fuel and oil mixture to correspond with the predetermined range the one or more predetermined portions may be added between measurements of the viscosity of the fuel and oil mixture. A corresponding viscosity of the fuel and oil mixture may include the measured viscosity of the fuel and oil mixture corresponds with the predetermined range of a combined viscosity. For example, a predetermined portion of fuel may be 0.5 fl. oz. of fuel. If a combined viscosity is determined to be 0.95 cSt with a predetermined range of ±0.1 cSt and the viscosity of the fuel and oil mixture is 1.12 cSt, then a predetermined portion of fuel may be added. The fuel pump 136 may add 0.5 fl. oz. of fuel to the fuel and oil mixture from the fuel reservoir 142. The 0.5 fl. oz. predetermined portion of fuel may be added to the fuel and oil mixture and the viscosity may be remeasured by the sensor module 110. The sensor module 110 may measure that the viscosity of the fuel and oil mixture is 1.08 cSt, which is still does not correspond with the predetermined range. The fuel pump 136 may then add a second 0.5 fl. oz. of fuel to the fuel and oil mixture from the fuel reservoir 142. The 0.5 fl. oz. predetermined portion may be added to the fuel and oil mixture and the viscosity may again be remeasured by the sensor module 110. The sensor module 110 may measure that the viscosity of the fuel and oil mixture as 1.03 cSt, which corresponds with the predetermined range, ceasing additions of predetermined portions of fuel from being added to the fuel and oil mixture.

The oil reservoir 144 may store a portion of oil that may be added to the fuel and oil mixture. The oil reservoir 144 may store the same or similar oil as used when making the fuel oil mixture for the fuel tank 130. The oil may be an unadulterated oil, which may include the oil that has not been premixed with the fuel. For example, a user may create the fuel and oil mixture from a first fuel and a first oil and fill the oil reservoir 144 with the first fuel. The fuel and oil mixture may be put into the fuel tank 130. An additional portion of the unadulterated first oil (which has not been mixed with the first fuel) may be put into the oil reservoir 144.

In various embodiments, the additional portion of the unadulterated oil may include a predetermined portion of oil. The predetermined portion of oil may include adding a measured amount of oil to the fuel and oil mixture. If the viscosity of the fuel and oil mixture does not correspond with the predetermined range, then one or more predetermined portions of oil may be added until the viscosity of the fuel and oil mixture corresponds with the predetermined range. To cause the fuel and oil mixture to correspond with the predetermined range the one or more predetermined portions may be added between measurements of the viscosity of the fuel and oil mixture. A corresponding viscosity of the fuel and oil mixture may include the measured viscosity of the fuel and oil mixture being within the predetermined range of a combined viscosity. For example, a predetermined portion of oil may be 0.1 fl. oz. of oil. If a combined viscosity is determined to be 0.95 cSt with a predetermined range of ±0.1 cSt and the viscosity of the fuel and oil mixture is 0.81 cSt, then a predetermined portion of oil may be added. The oil pump 138 may add 0.1 fl. oz. portion of oil to the fuel and oil mixture from the oil reservoir 144. The 0.1 fl. oz. predetermined portion of oil may be added to the fuel and oil mixture and the viscosity may be remeasured by the sensor module 110. The sensor module 110 may measure that the viscosity of the fuel and oil mixture is 0.83 cSt, which still does not correspond with the predetermined range. The oil pump 138 may then add a second 0.1 fl. oz. portion of oil to the fuel and oil mixture from the oil reservoir 144. The 0.1 fl. oz. predetermined portion may be added to the fuel and oil mixture and the viscosity may be again be remeasured by the sensor module 110. The sensor module 110 may measure that the viscosity of the fuel and oil mixture is 0.86 cSt, which corresponds with the predetermined range, ceasing additions of predetermined portions of oil from being added to the fuel and oil mixture.

Figure 2:
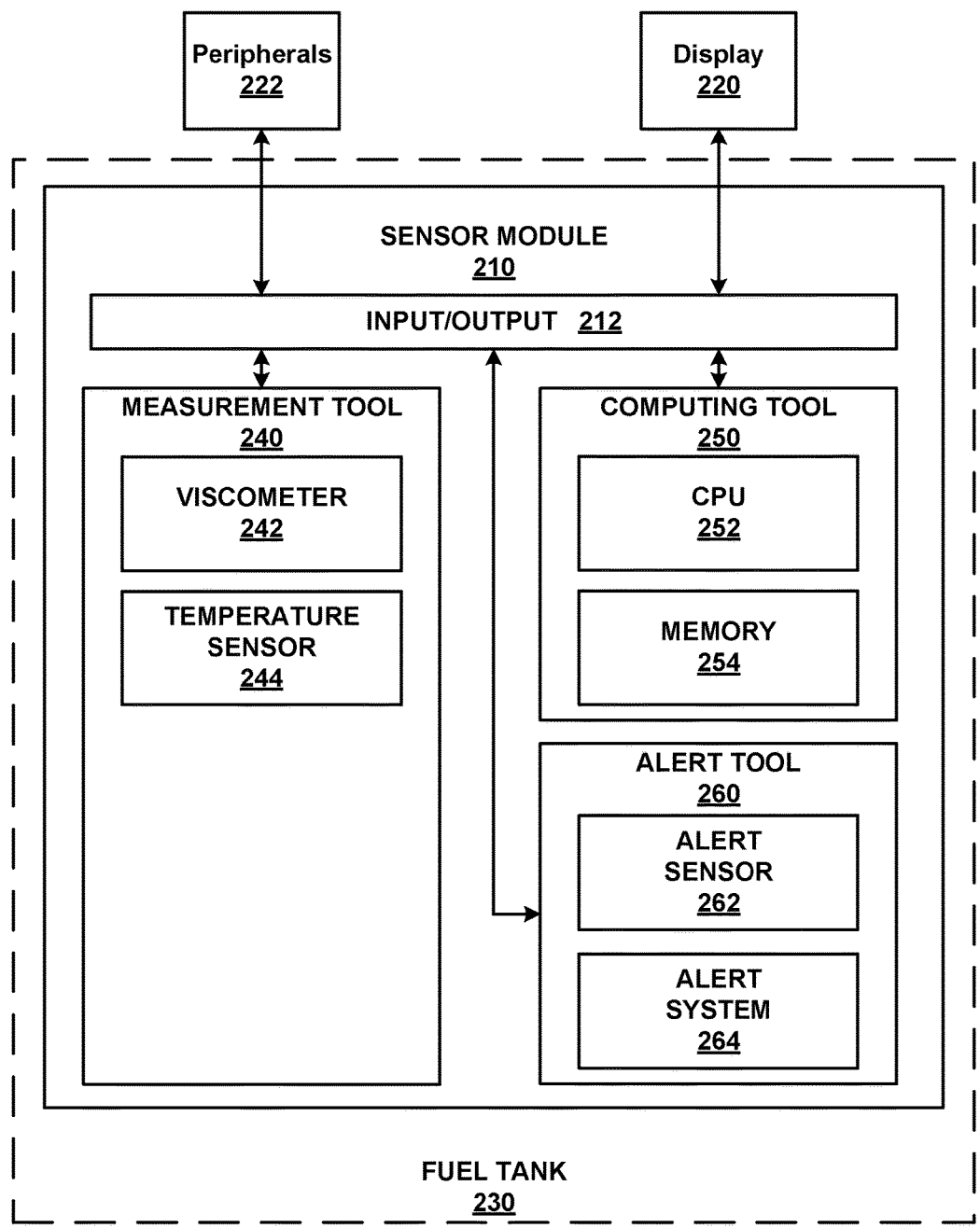
FIG. 2 depicts an illustration of components of a sensor module, according to various embodiments.

FIG. 2 depicts an illustration of components of a sensor module, according to embodiments. The components of the sensor module 210 may include an input/output 212, which may communicatively couple the display 220 to the sensor module 210. The input/output 212 of the sensor module may communicatively couple a measurement tool 240, a computing tool 250, and an alert tool 260. The measurement tool 240 may include a viscometer 242 and a temperature sensor 244. The computing tool 250 may include a central processing unit (CPU) 252 and a memory 254. The alert tool 260 may include an alert sensor 262 and an alert system 264. The sensor module 210 may be located within or placed within a fuel tank 230. The fuel tank 230 may contain a fuel and oil mixture, and the sensor module may determine if the fuel and oil mixture corresponds with or does not correspond with a predetermined range (range, predetermined range).

The measurement tool 240, such as the viscometer 242 and the temperature sensor 244, may measure the viscosity and the temperature of the fuel and oil mixture within the fuel tank 230. The viscometer 242 may continuously measure the viscosity of the fuel and oil mixture. The temperature sensor 244 may continuously measure the temperature of the fuel and oil mixture. For example, the fuel and oil mixture may be recorded by the viscometer 242 as having a viscosity of 1.02 cSt, and the temperature sensor 244 may record a temperature of 40° C. The recorded viscosity and temperature may be gathered by the input/output 212, which may send the viscosity and the temperature to the computing tool 250, and the alert tool 260.

In various embodiments, the viscometer 242 of the measurement tool 240 may measure the viscosity in 0.03 cSt increments. If the viscometer 242 may measure a viscosity at 0.03 cSt increments, the fuel:oil ratio may be calculated to the 3 parts out of 100 parts, or 0.03% of oil in the fuel and oil mixture. By precisely calculating the viscosity of the fuel and oil mixture, the actual fuel:oil ratio or percentage of oil may be displayed to the user. The user may then change the fuel:oil ratio based on the display. For example, the fuel:oil ratio of the engine may require a 40:1 fuel:oil ratio; if a fuel and oil mixture is 38:1, the user may add oil to the fuel tank to correct the fuel:oil ratio.

The computing tool 250 such as the CPU 252 and the memory 254 may receive the measured viscosity of the fuel and oil mixture from the measurement tool 240 and calculate the actual fuel:oil ratio of the fuel and oil mixture. The CPU 252 may be used to perform the calculations of the computing tool 250. The memory 254 may store the calculations to be carried out by the CPU 252 of the computing tool 250. The computing tool 250 may receive input from the display 220 regarding the fuel and oil mixture within the fuel tank 230. The input received on the display may include the user inputting an oil viscosity of an oil, and a fuel viscosity of a fuel. The input/output 212 may receive from the display 220 information that may contain the octane of the fuel, the type of oil, and the fuel:oil ratio of the engine. The computing tool 250 may use the temperature from the temperature sensor 244 and the information from the user to determine a calculated fuel:oil viscosity and a predetermined range of acceptable viscosities. For example, if the fuel has a viscosity of 0.6 cSt, the viscosity of the oil is 71 cSt, the temperature is 40° C., and the fuel:oil ratio for the engine is 20:1, then the calculated viscosity may be 1.025 cSt. The calculated viscosity may be sent to the alert tool 260 through the input/output 212.

The computing tool 250 may be in communication with or connected through the input/output 212 to peripherals 222 that the user may use to interact with the display 220. The peripherals 222 may include computer keyboards, computer mice, touch screens, a barcode scanner, image scanners, and microphones. The peripherals 222 may be used to input information to the computing tool 250 for determining the fuel:oil ratio. For example, a user may use a keyboard to input the viscosity of the fuel, the viscosity of the oil, and the fuel:oil ratio of the engine. The peripherals 222 may be included within the display 220. For example, peripherals 222 being a touch screen may be within the display 220. The touchscreen peripheral 220 may receive input from a user that is communicated through the input/output 212 to the computing tool 250.

In various embodiments, the computing tool 250 may register and calculate a predetermined range (i.e. a range of interest) that the fuel and oil mixture may be within. If the fuel and oil mixture corresponds with the predetermined range, an alert may not be generated. The predetermined range may be used to determine if the fuel and oil mixture is correct for the fuel:oil ratio of the engine. For example, if the viscosity of the fuel and oil mixture at a temperature is 0.75 cSt, and the calculated viscosity from the fuel and the oil at the temperature is 0.78 cSt with a predetermined range of ±0.05 cSt, then an alert may not be generated.

In various embodiments, the computing tool 250 may calculate the fuel:oil ratio as a percentage of oil within the fuel of the fuel and oil mixture. For example, a 100:1 fuel:oil ratio is a 1% oil mixture. The calculated viscosity of a 100:1 fuel:oil ratio would be the same or substantially similar to a 1% oil mixture. The computing tool 250 may use the percentages to determine if the fuel and oil mixture corresponds with a predetermined range. For example, if the actual measured fuel and oil mixture is 1.85% oil, and the actual fuel:oil ratio is a 2% oil mixture with a ±0.2% predetermined range, then the alert tool 260 may not generate an alert because the 1.85% oil mixture corresponds with the predetermined range.

In various embodiments, the computing tool 250 may also determine a second threshold where a near 0% oil mixture is present. If the fuel:oil ratio is near 0% oil, a second threshold may be reached generating a second alert from the alert tool 260. For example, the predetermined range of a fuel:oil ratio may be a 0% with a +0.2% range. If the fuel and oil mixture contains a 0.1% oil mixture, then the second threshold may be reached, and the second alert may be generated.

The alert tool 260 which includes the alert sensor 262 and the alert system 264 may receive the actual fuel:oil ratio from the computing tool 250 and generate an alert if the fuel:oil ratio does not correspond with the calculated range. The alert generated from the alert system 264 may be sent through the input/output 212 to the display 220. The display 220 may display the actual fuel:oil ratio to the user and issue an alert if the fuel:oil ratio does not correspond with the calculated range. For example, the calculated fuel:oil ratio may be 1.025 cSt with a predetermined range of ±0.1 cSt. If the actual fuel:oil ratio is 1.02 cSt an alert may not be generated because the actual fuel:oil ratio corresponds with the predetermined range. In an additional example, the calculated fuel:oil ratio may be 1.0 cSt with a predetermined range of ±0.1 cSt. If the actual fuel:oil ratio is 1.15 cSt, an alert may be generated because the ratio of the fuel and oil mixture does not correspond with the predetermined range.

In various embodiments, the alert tool 260 may generate a second alert if the alert sensor 262 determines that the actual fuel:oil ratio does not correspond with a second predetermined range. The determination of the second predetermined range may include that oil may have not been added to the fuel and oil mixture. For example, if the viscosity of the fuel is 0.6 cSt, and the actual fuel and oil mixture has a viscosity of 0.6 cSt, then oil may have not been added to the mixture.

In various embodiments, the display 220 may be a GUI. The GUI may display the fuel:oil ratio of the fuel and oil mixture. The GUI may include peripherals 222 that the user may interact with to provide information to the computing tool 250. The information may include the type of the fuel, the type of the oil, and the fuel:oil ratio of the engine. The GUI may receive an alert through the input/output 212 from the alert tool 260.

In various embodiments, the alert system 264 may shut off the engine if the fuel:oil ratio within the fuel tank 230 does not correspond with the calculated range. If the measured viscosity of the fuel and oil mixture does not correspond with the predetermined range, then the engine may be shut off to prevent the engine from being damaged. The measured viscosity may be the viscosity measured by the viscometer. For example, where the calculated fuel:oil ratio is 1.0 cSt with a predetermined range of ±0.1 cSt, if the measured viscosity of the fuel and oil mixture is 1.15 cSt, then the engine may be shut off to prevent damage to the engine.

FIG. 3 depicts tables of the combined viscosity of a fuel:oil ratio with respect to temperature, according to embodiments. The fuel:oil ratio may be calculated and stored as a table. The table may be a lookup table that a computer may store and access to determine if the fuel and oil mixture does not correspond with a predetermined range of a measured fuel:oil ratio. The predetermined range of the fuel:oil ratio may be calculated and stored on the lookup table. The calculated fuel:oil ratio may be calculated as a combined viscosity. To determine if the fuel and oil mixture does not correspond with the predetermined range, a combined viscosity may be calculated for the fuel and the oil based on a fuel:oil ratio. To calculate the viscosity of the fuel:oil ratio, a viscosity of the oil at two different temperatures may be known.

Two known oils with a fuel are used in determining the fuel:oil ratio: a first oil, Sinclair Artic Fire®, and a second oil, AMSOIL SABER®. Two measured viscosities of the oil are given on a material data safety sheet (MSDS) of the oils; Artic Fire® has a viscosity of 30.5 cSt at 40° C. and 6.17 cSt at 100° C., and AMSOIL SABER® has a viscosity of 71 cSt at 40° C. and 11.1 cSt at 100° C. The viscosity of gasoline or petrol fuels may range from 0.5-0.8 cSt at 40° C. and 100° C. depending on the manufacturer or refiner of the fuel. A viscosity of 0.6 cSt may be used at both 40° C. and 100° C. for calculating the combined viscosity. Five fuel:oil ratios of the table may be used to calculate the combined viscosity. The fuel ratios may include a 20:1, a 40:1, a 50:1, an 80:1, and a 100:1 fuel:oil ratio. The combined viscosities of the fuel and both of the oils were calculated at each of the temperatures and the fuel:oil ratios. For example, the combined viscosity of a 20:1 fuel:oil ratio of ARTIC FIRE® at 40° C. is 0.878 cSt. In an additional example, the combined viscosity of a 20:1 fuel:oil ratio of SABER® at 40° C. is 1.025 cSt.

In various embodiments, the predetermined range may be calculated dynamically from the combined viscosity. The dynamic fuel:oil ratio range of the viscosity may be a percentage difference from the combined viscosity. The dynamic fuel:oil ratio range may be adjusted based on the needs of the user. The percentage difference of the dynamic fuel:oil ratio range can be calculated from a percentage deviation or dynamic range of the combined viscosity. For example, if the combined viscosity of a 20:1 fuel:oil ratio of Sinclair ARTIC FIRE® at 40° C. is 0.878 cSt, then a 10% dynamic range may be ±0.087 cSt. If the actual fuel and oil mixture viscosity is between 0.965 cSt and 0.792 cSt, the measured viscosity may not cause an alert system to generate an alert. In an additional example, if the combined viscosity of a 20:1 fuel:oil ratio of SABER® at 40° C. is 1.025 cSt, then a 10% dynamic range may be ±0.1 cSt. If the actual fuel and oil mixture viscosity is between 1.125 cSt and 0.903 cSt, the measured viscosity may not cause an alert system to generate an alert.

In various embodiments, additional two-stroke oils may be updated into the lookup table. The lookup table may be updated by the user if an oil is not currently stored on the table. The lookup table may be stored within the memory of the computing tool. The lookup table may be accessed through the internet if the sensor module is wirelessly enabled. The user may input a first viscosity of the oil at a first temperature and a second viscosity of the oil at a second temperature. By inputting the two viscosities at two temperatures, the viscosity of the oil at various temperatures may be calculated. The viscosities at various temperatures can be used to determine if the fuel and oil mixture corresponds with the predetermined range. For example, an oil with a viscosity of 65 cSt at 40° C. and 9 cSt at 100° C. would have a viscosity of approximately 28.47 cSt at 60° C.

In various embodiments, the lookup table may be updated through the internet. The lookup table stored within the memory of the computing device may be updated. Updating the lookup table may include adding oils to the lookup table. For example, the lookup table may connect to the internet wirelessly and if a new oil can be added to the lookup table, the computing tool may download and add the new oil to the lookup table.

Figure 4:
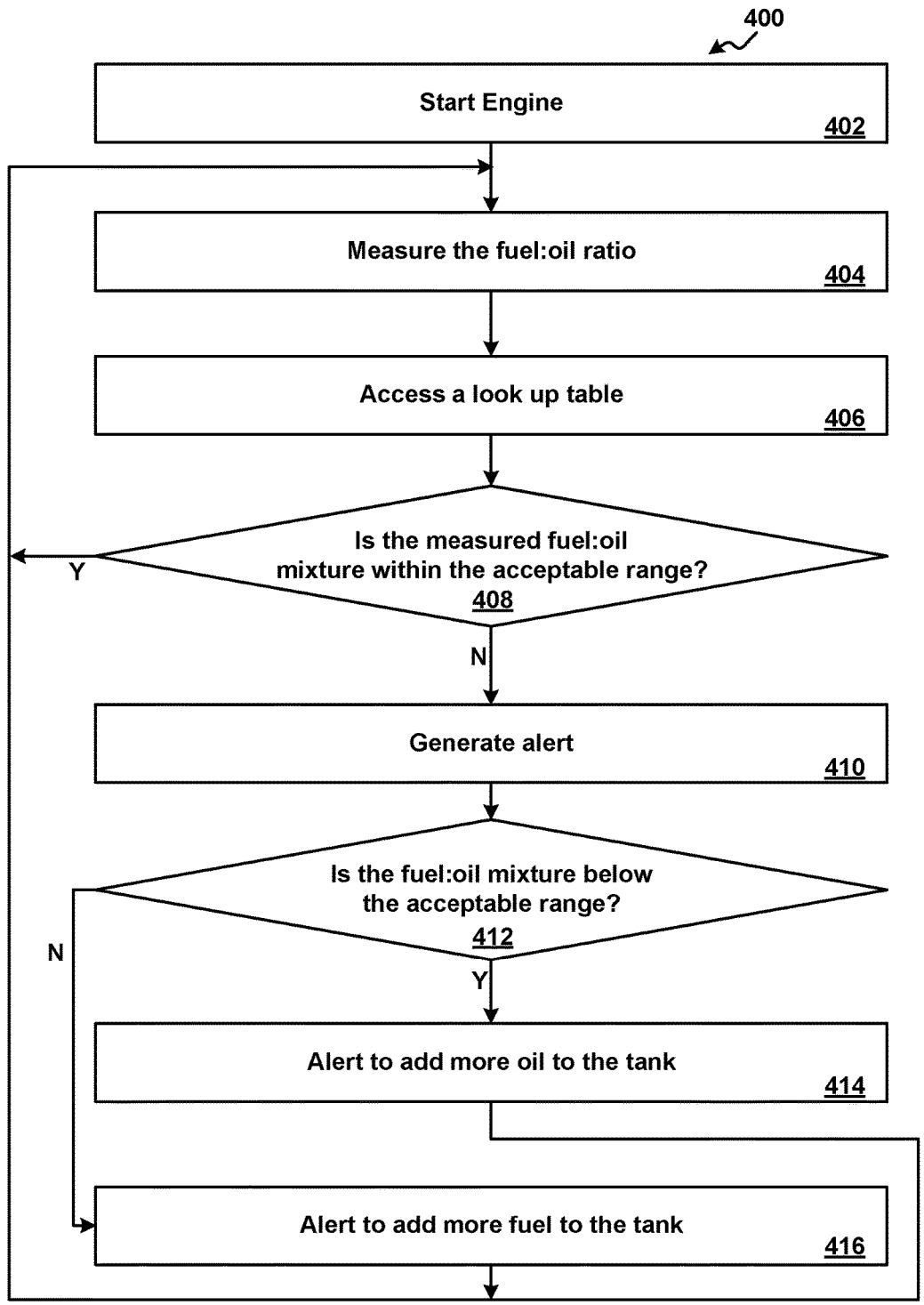
FIG. 4 depicts a flowchart of monitoring a fuel to oil ratio within a fuel tank, according to various embodiments.

FIG. 4 depicts a flowchart of a method that monitors a fuel to oil ratio within a fuel tank, according to embodiments. A sensor module may be equipped with a viscometer and a temperature sensor to determine the fuel:oil ratio of a fuel and oil mixture. The sensor module may measure the viscosity and the temperature of the fuel and oil mixture. The measured fuel and oil mixture may be compared to a lookup table which stores a calculated combined viscosity of a fuel:oil ratio. The calculated combined viscosity includes a fuel, an oil, a temperature, and a fuel:oil ratio. Each fuel, oil, temperature, and fuel:oil ratio may be stored on the lookup table to be able to compare the viscosity of the fuel and oil mixture with the calculated combined viscosity. If the viscosity of the measured fuel:oil ratio does not correspond with a predetermined (acceptable) range of the calculated combined viscosity, then an alert may be generated to a user. The alert may include informing the user that the fuel and oil mixture does not correspond with the predetermined range of the calculated combined viscosity, and may include informing the user to add more fuel or more oil. The method 400 may be repeated to ensure that the fuel:oil ratio remains corresponding with the predetermined range. The predetermined range may include an upper limit and a lower limit of the measured viscosity.

In operation 402, an engine is started. The engine may be a two-stroke engine that includes a fuel tank. The fuel tank may include a sensor module that monitors the fuel and oil mixture within the fuel tank. The engine may power the machine the engine is connected to and the sensor module. The sensor module may also be powered externally. In starting the engine, the sensor module may require the user to select or input a fuel:oil ratio based on the two-stroke engine. Some two-stroke engines require a 20:1 fuel:oil ratio, while others require an 80:1 fuel oil ratio. The user may need to select the fuel:oil ratio before the sensor module may alert the user of the fuel and oil mixture not corresponding with a predetermined range.

In operation 404, the fuel:oil ratio of the fuel and oil mixture within the fuel tank is measured. The fuel and oil mixture is measured by the sensor module. The sensor module may measure the viscosity and the temperature of the fuel and oil mixture. For example, the sensor module may detect that the fuel and oil mixture, where the oil is AMSOIL SABER®, has a viscosity of 0.82 cSt at a temperature of 40° C. In an additional example, the sensor module may detect that the fuel and oil mixture, where the oil is Sinclair Artic Fire®, has a viscosity of 0.65 cSt at 100° C.

In operation 406, a lookup table is accessed. The lookup table may include the combined viscosity of the fuel:oil ratios of various two-stroke engine oils and fuels. The lookup table may be accessed by the sensor module or stored within the sensor module to determine if the viscosity of the fuel and oil mixture does not correspond with a predetermined range of the calculated combined viscosity. For example, the calculated combined viscosities of AMSOIL SABER® may be accessed at 40° C. for all of the fuel:oil ratios. At a 40:1 ratio the combined viscosity of AMSOIL SABER® at 40° C. may be approximately 0.794 cSt. In an additional example, the calculated combined viscosities of Sinclair Artic Fire® may be accessed at 100° C. for all of the fuel:oil ratios. At a 50:1 ratio the combined viscosity of Sinclair Artic Fire® at 100° C. may be approximately 0.643 cSt.

In operation 408, the fuel and oil mixture is determined to correspond with the predetermined rang or not correspond with the predetermined range of the calculated combined viscosity. The predetermined range of the calculated combined viscosity may be determined. If the fuel:oil ratio does not correspond with the predetermined range, then the method 400 may progress to operation 410. For example, the measured fuel and oil mixture may include an oil of AMSOIL SABER® at 40° C. with a viscosity of 0.82 cSt. If the fuel:oil ratio of the two-stroke engine is a 20:1, the combined viscosity may be 1.025 and the predetermined range may be ±0.1 cSt. Since the viscosity of the measured fuel and oil mixture is 0.82 cSt, the fuel:oil ratio does not correspond with the predetermined range of the combined viscosity. In an additional example, the measured fuel and oil mixture may include an oil of Sinclair Artic Fire® at 100° C. with a viscosity of 0.65 cSt. If the fuel:oil ratio of the two-stroke engine is a 20:1, the combined viscosity may be 0.712 cSt and the predetermined range may be ±0.02 cSt. Since the viscosity of the measured fuel and oil mixture is 0.65 cSt, the fuel:oil ratio does not correspond with the predetermined range of the combined viscosity.

If the fuel:oil ratio corresponds with the predetermined range, then the method 400 may return to operation 404 where the fuel:oil ratio is measured. For example, the measured fuel and oil mixture may include an oil of AMSOIL SABER® at 40° C. with a viscosity of 0.82 cSt. If the fuel:oil ratio of the two-stroke engine is a 40:1, then the combined viscosity calculated of the fuel:oil ratio may be 0.794 and the predetermined range may be ±0.05 cSt. Since the viscosity of the measured fuel and oil mixture is 0.82 cSt, the fuel:oil ratio corresponds with the predetermined range of the combined viscosity. In an additional example, the measured fuel and oil mixture may include an oil of Sinclair Artic Fire® at 100° C. with a viscosity of 0.65 cSt. If the fuel:oil ratio of the two-stroke engine is a 50:1, the combined viscosity may be 0.643 cSt and the predetermined range may be ±0.01 cSt. Since the viscosity of the measured fuel and oil mixture is 0.65 cSt, the fuel:oil ratio corresponds with the predetermined range of the combined viscosity.

In operation 410, an alert may be generated by an alert tool if the fuel and oil mixture does not correspond with the predetermined range. The alert may include informing the user that the fuel and oil mixture does not correspond with the predetermined range. For example, the measured fuel and oil mixture may include an oil of AMSOIL SABER® at 40° C. with a viscosity of 0.82 cSt. If the fuel:oil ratio of the two-stroke engine is a 20:1, then the combined viscosity may be 1.025 and the predetermined range may be ±0.1 cSt. Since the viscosity of the measured fuel and oil mixture is 0.82 cSt, then an alert may be generated.

In various embodiments, the alert may include an audible alarm. If the alert is generated, then the audible alarm may generate a noise to the user that the viscosity of the fuel and oil mixture does not correspond with the predetermined range. For example, if the calculated viscosity is 1.0 cSt with a predetermined range of ±0.1 cSt and the measured viscosity of the fuel and oil mixture is 0.89 cSt, then the audible alarm may generate and output a noise to the user.

In various embodiments, the alert may include a visual alarm. If the alert is generated, then the visual alarm may generate a visual indicator to the user that the viscosity of the fuel and oil mixture does not correspond with the predetermined range. Examples of visual indicators may include a light that is illuminated, or a warning message displayed to the user on a display. For example, if the calculated viscosity is 1.0 cSt with a predetermined range of ±0.1 cSt and the measured viscosity of the fuel and oil mixture is 0.89 cSt, then the visual alarm may generate and output a visual indicator to the user.

In operation 412, the fuel and oil mixture is determined if fuel oil mixture is below the predetermined range. The viscosity may be determined based on the viscosity of the fuel, the oil, a calculated viscosity of the fuel:oil ratio, and the temperature. If the fuel and oil mixture does not correspond with the predetermined range and not viscous enough, the oil of the fuel and oil mixture may be too low meaning the engine may not be properly lubricated. If the mixture does not correspond with the predetermined range and too viscous, then the oil in the fuel and oil mixture may be too high causing burn rate problems and exhaust fumes. The determination may be used to determine if the fuel:oil ratio of the fuel and oil mixture is above or below the predetermined range. If the fuel and oil mixture is below the predetermined range (i.e. not enough oil), the method may progress to operation 414 where an alert informs the user to add more oil to the tank. For example, the measured fuel and oil mixture may include an oil of AMSOIL SABER® at 40° C. with a viscosity of 0.82 cSt. If the fuel:oil ratio of the two-stroke engine is a 20:1, the combined viscosity may be 1.025 and the predetermined range may be ±0.1 cSt. Since the viscosity of the measured fuel and oil mixture is 0.82 cSt, the fuel:oil ratio does not correspond with the predetermined range of the combined viscosity and below the predetermined range. In an additional example, the measured fuel and oil mixture may include an oil of Sinclair Artic Fire® at 100° C. with a viscosity of 0.65 cSt. If the fuel:oil ratio of the two-stroke engine is a 20:1, the combined viscosity may be 0.712 cSt and the predetermined range may be ±0.02 cSt. Since the viscosity of the measured fuel and oil mixture is 0.65 cSt, the fuel:oil ratio does not correspond with the predetermined range of the combined viscosity and below the predetermined range.

If the fuel and oil mixture is above the predetermined range (i.e. too much oil) the method may progress to operation 416 where an alert informs the user to add more fuel to the tank. For example, the measured fuel and oil mixture may include an oil of AMSOIL SABER® at 40° C. with a viscosity of 1.13 cSt. If the fuel:oil ratio of the two-stroke engine is a 20:1, the combined viscosity may be 1.025 and the predetermined range may be ±0.1 cSt. Since the viscosity of the measured fuel and oil mixture is 1.13 cSt, the fuel:oil ratio does not correspond with the predetermined range of the combined viscosity and above the predetermined range. In an additional example, the measured fuel and oil mixture may include an oil of Sinclair Artic Fire® at 100° C. with a viscosity of 0.65 cSt. If the fuel:oil ratio of the two-stroke engine is an 80:1, the combined viscosity may be 0.627 cSt and the predetermined range may be ±0.02 cSt. Since the viscosity of the measured fuel and oil mixture is 0.65 cSt, the fuel:oil ratio does not correspond with the predetermined range of the combined viscosity and above the predetermined range.

In operation 414, an alert is generated, in response to the fuel oil ratio being below the predetermined range, and sent to the user to add more oil to the tank. If the fuel:oil ratio is below the predetermined range, then an alert may be sent to the user informing the user to add more oil to the tank. For example, the viscosity of a fuel and oil mixture of Sinclair Artic Fire® at 40° C. with a fuel:oil ratio of 50:1 may include a combined viscosity of 0.703 cSt with an predetermined range of ±0.02 cSt. If the fuel and oil mixture has a viscosity of 0.68 cSt, then the fuel and oil mixture does not correspond with and below the predetermined range. The alert may be generated and sent to the user to inform the user to add more oil.

In various embodiments, a second alert may be generated if the fuel and oil mixture has a viscosity low enough that the user may have not added oil. A threshold may be added to the combined viscosity. If the viscosity of the fuel and oil mixture is below the threshold a second alert may be generated and sent to the user to inform the user that oil may have not been added to the mixture. For example, the viscosity of a fuel may be 0.6 cSt, which may set a second threshold at 0.62 cSt for a fuel and oil mixture of Sinclair Artic Fire® at 40° C., and a fuel:oil ratio of 50:1. If the viscosity of the fuel and oil mixture is below 0.62 cSt, then the second alert may be sent to the user.

In operation 416, an alert is generated, in response to the fuel oil ratio being above the predetermined range, and sent to the user to add more fuel to the tank. If the fuel:oil ratio is above the predetermined range, then an alert may be sent to the user informing the user to add more fuel to the tank. For example, the viscosity of a fuel and oil mixture of Sinclair Artic Fire® at 40° C. with a fuel:oil ratio of 50:1 may include a combined viscosity of 0.703 cSt with an predetermined range of ±0.02 cSt. If the fuel and oil mixture has a viscosity of 0.73 cSt, then the fuel and oil mixture is above and does not correspond with the predetermined range. The alert may be generated and sent to the user to inform the user to add more fuel.

In various embodiments, the alert to add more oil or fuel to the tank may include shutting off the engine. If the viscosity of the fuel and oil mixture does not correspond with the accepted range, then the engine may be shut off to prevent damage to the engine. For example, the calculated combined viscosity of the viscosity of a fuel and oil mixture of Sinclair Artic Fire® at 40° C. and a fuel:oil ratio of 50:1 may include a combined viscosity of 0.703 cSt. The combined viscosity may include a predetermined range of ±0.02 cSt. If the fuel and oil mixture has a viscosity of 0.66 cSt, then the fuel and oil mixture is below the predetermined range. The alert may be generated and sent to the user to inform the user to add more oil and the engine may be shut off to prevent damage to the engine.

The present invention may be a system, a method, and/or a computer program product. The computer program product may include a computer readable storage medium (or media) having computer readable program instructions thereon for causing a processor to carry out aspects of the present invention.

The computer readable storage medium may be a tangible device that may retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein may be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that may direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A system for determining a fuel to oil mixture ratio comprising:
   a computing tool having:
      a memory, and
      a processor device communicatively coupled to the memory;
      the processor device is configured to:
         select a fuel to oil ratio of a first motor for a fuel and oil mixture,
         calculate a combined viscosity of the fuel and oil mixture,
         determine a predetermined range of the fuel to oil ratio and wherein the fuel is ignited by a spark plug in the first motor; and
   a measurement tool that is communicatively coupled to the computing tool and configured to:
      measure a measured viscosity of the fuel to oil mixture within a fuel tank; and
   a graphical user interface configured to:
   alert a user through the graphical user interface that the measured viscosity of the ratio of the fuel to oil mixture does not correspond with the predetermined range.

* * * * *